(12) United States Patent  
Bowersox et al.

(10) Patent No.: US 6,530,278 B1
(45) Date of Patent: Mar. 11, 2003

(54) ULTRASONIC TESTING OF TANK CAR WELDS

(76) Inventors: Matthew D. Bowersox, 51 Woodlawn Ave., Milroy, PA (US) 17063; Jerry H. Spigelmyer, 407 Eighth Ave., Burnham, PA (US) 17009; Daniel L. Yoder, 20 Quail Dr., McVeytown, PA (US) 17051; Dane E. Hackenberger, R.R. 1 Box 876, Mifflintown, PA (US) 17059; Sherrill R. Harris, 342 Green Grove Rd., Spring Mills, PA (US) 16875-9738; William P. Waldron, 938 Bayberry Dr., State College, PA (US) 16801; Frederick R. Hoar, R.D. 1 Box 125, 9 Royal St., Reedsville, PA (US) 17084

( * ) Notice: Subject to any disclaimer, the term of this patent is extended or adjusted under 35 U.S.C. 154(b) by 0 days.

(21) Appl. No.: 09/566,331

(22) Filed: May 8, 2000

Related U.S. Application Data
(60) Provisional application No. 60/135,390, filed on May 21, 1999.

(51) Int. Cl.[7] ............................................. G01N 29/26
(52) U.S. Cl. .......................................... 73/623; 73/640

(58) Field of Search ........................ 73/622, 623, 637, 73/620, 640

(56) References Cited

U.S. PATENT DOCUMENTS 3,741,003 A * 6/1973 Gunkel ........................ 73/637
3,934,457 A * 1/1976 Clark et al. .................. 73/637
4,375,165 A * 3/1983 De Sterke ..................... 73/622

* cited by examiner

Primary Examiner—John E. Chapman
(74) Attorney, Agent, or Firm—Carmen Santa Maria; McNees Wallace & Nurick, LLC

(57) ABSTRACT

An ultrasonic testing system for testing the circumferential girth welds of a tank for defects utilizes a probe trolley to which six probes are attached. The probe trolley is clamped to a drive unit which runs upon a track that is removably attached to the interior surface of the tank. The track is positioned so that the probe trolley travels over the weld as the drive unit negotiates the track. Coupling fluid is supplied to the probe trolley so that a layer of coupling fluid exists between the probes and the tank interior surface adjacent to the weld. Ultrasonic beams emitted by the probe travel through the coupling fluid, into the tank wall and weld and are reflected. Data from the probes is directed to a processor where it is analyzed, displayed and stored.

21 Claims, 8 Drawing Sheets

ULTRASONIC TESTING OF TANK CAR WELDS

This application claims priority from U.S. Provisional App. No. 60/135,390, filed May 21, 1999.

BACKGROUND OF THE INVENTION

The present invention relates generally to ultrasonic testing and inspection of welding seams, and, more particularly, to a system for performing automated ultrasonic testing and inspection of the welds of railroad tank cars.

Federal regulations (HM-201) directed to the testing of welds in railroad tank cars were promulgated by the Department of Transportation (DOT) in 1995. More specifically, HM-201 guidelines prohibit the use of hydrostatic tank testing and, instead, require that welds in high-stress areas be tested for structural integrity using an approved non-destructive testing technique. The DOT has identified the circumferential girth butt-welds in the bottom portion of the tank shells of railroad tank cars as high-stress areas. As a result, these welds must be tested and inspected for subsurface flaws or defects via an approved non-destructive testing technique. Ultrasonic flaw detection is one of the approved non-destructive testing techniques.

Ultrasonic flaw detection or testing typically utilizes a probe or transducer that passes in close proximity along the front surface of the weld being tested. The transducer communicates with the weld via a coupling fluid such as water or gel. The probe imparts high-frequency sound waves into the weld through the fluid. The sound waves are reflected back to the probe from the back surface of the weld or internal flaws. Monitoring of this reflection of the sound waves is used to determine weld characteristics such as thickness and the presence of defects or flaws in the form of discontinuities.

Automated ultrasonic flaw detection systems, whereby motion is induced between the weld being tested and one or more probes, have been in use for over 35 years in industries such as the welded tube industry (i.e. pipelines, structural steel, etc.). Patents illustrating this technology include U.S. Pat. No. 5,585,565 to Glascock et al.; U.S. Pat. No. 5,174,155 to Sugimoto; U.S. Pat. No. 4,627,289 to Fukuda et al.; U.S. Pat. No. 4,375,165 to de Sterke and U.S. Pat. No. 4,305,297 to Ries et al. All of these patents, however, illustrate automated ultrasonic testing systems that operate on the exterior surface of the pipe being tested. When ultrasonic testing is used, the welds of railroad tank cars must be scanned from inside, that is, on the interior surface, of the tank.

In the past, ultrasonic testing of railroad tank cars has been performed manually by technicians utilizing hand-held transducers or probes. Such ultrasonic testing of the tank car welds requires that the technician use multiple scanning patterns by which the proximity and angle of the probe, with respect to the weld, is varied. As a result, manual scanning is expensive and time consuming. Companies are motivated to minimize the cost of tank car testing for obvious reasons. Furthermore, in order to maximize utilization and therefore profits, companies desire that their tank cars be returned to service as quickly as possible. As such, it is desirable to provide an ultrasonic testing system for tank cars that operates quickly.

In addition, the accuracy of the results obtained in manual ultrasonic testing depends a great deal upon the skill of the technician. As such, it may be difficult to obtain consistent and reliable test results. In other words, two technicians may obtain different results even though they scanned the same weld. It is therefore desirable to provide an ultrasonic testing system that consistently provides effective performance.

Accordingly, it is an object of the present invention to provide an ultrasonic testing system for tank car welds that is automated.

It is another object of the present invention to provide an ultrasonic testing system for tank cars that will test the circumferential girth butt-welds in the bottom portion of the tank car shells.

It is another object of the present invention to provide an ultrasonic testing system for tank cars that is inexpensive and operates quickly.

It is still another object of the present invention to provide an ultrasonic testing system for tank cars that consistently provides effective performance and reliable test results.

SUMMARY OF THE INVENTION

The present invention is directed to an ultrasonic testing system for inspecting the circumferential girth welds of a railroad tank car for internal or surface flaws or defects. The system includes a probe trolley to which six probes are mounted. The probe trolley is clamped to a drive unit that travels upon a track that is positioned on a surface adjacent to the weld being inspected. The track is attached to the inner surface of the tank in a removable fashion by magnetic mounts and is oriented to run parallel to the weld.

The probe trolley includes a top plate to which each of the probes is mounted via a probe mounting assembly. Each probe mounting assembly includes a bearing holder secured to the top plate with a bearing disposed therein. A piston is slidably received in the bearing and is connected to a probe shoe that holds the probe in a removable fashion. The probe is attached to a wedge prior to insertion into the probe shoe. The wedge holds the probe at the appropriate angle with regard to the thickness of the weld and the surface adjacent to the weld.

The probe shoes are mounted to the pistons by swivel balls and compression springs are utilized between the probes shoes and the bearing holders. Furthermore, coupling fluid is supplied to the probe shoes so that a layer of coupling fluid exists between the probes and the surface adjacent to the weld. As a result, the probe shoes float upon a layer of coupling fluid and ultrasonic beams emitted by the probes pass through the coupling fluid and into the tank wall and weld and are reflected therefrom.

A computer communicates with the probes so that data from the probes may be collected, analyzed, displayed and stored. By rotating the probe trolley 180° and performing a second scan or pass, the weld is effectively subjected to scanning by twelve probe positions or scanning patterns.

The following detailed description of embodiments of the invention, taken in conjunction with the appended claims and accompanying drawings, provide a more complete understanding of the nature and scope of the invention.

DESCRIPTION OF THE PREFERRED EMBODIMENT

Figure 1:
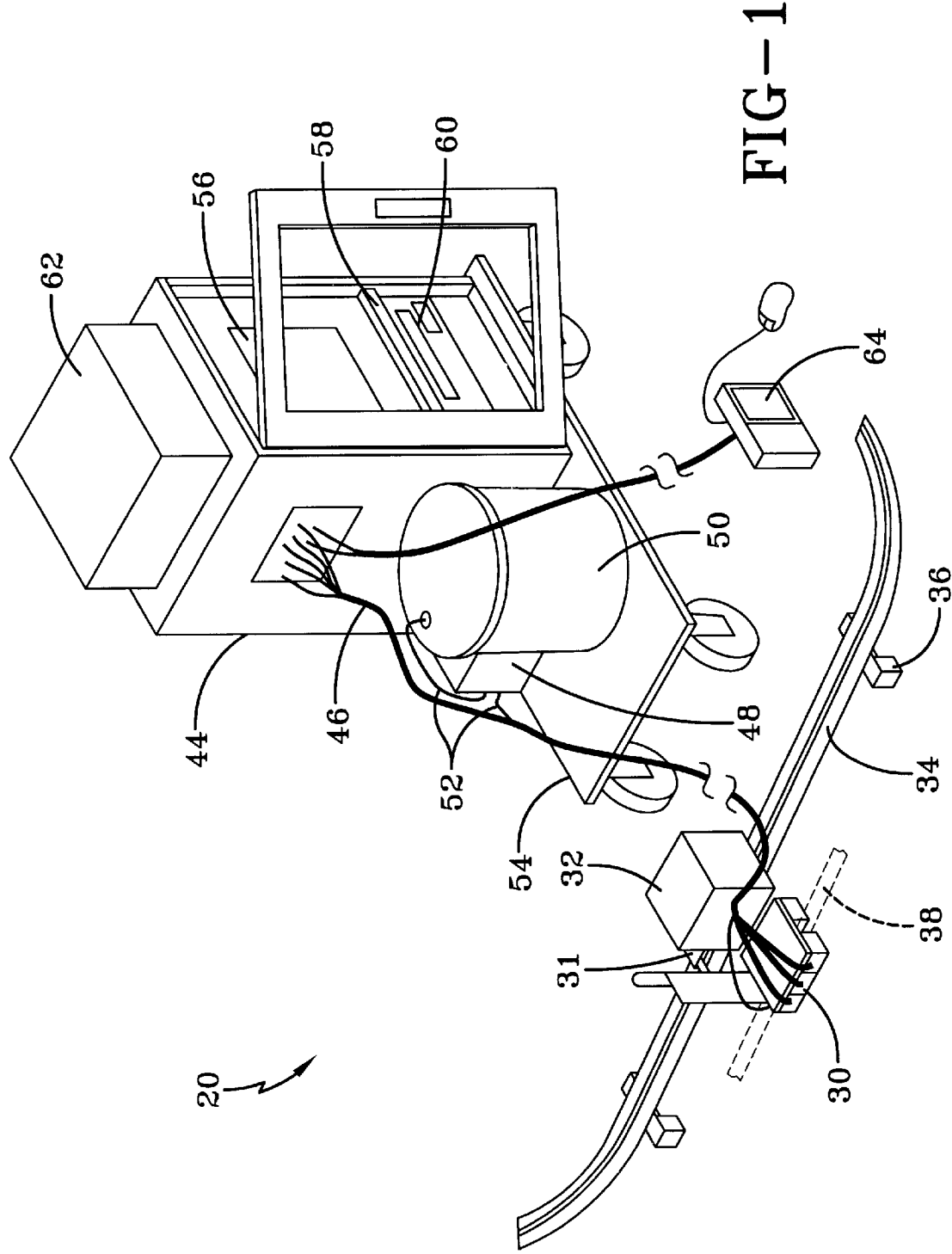
FIG. 1 is a perspective view of an embodiment of the ultrasonic testing system of the present invention.

With reference to FIG. 1, an embodiment of the ultrasonic testing system of the present invention is indicated generally at 20. The system includes a probe trolley 30 mounted by an adjustable clamping mechanism 31 to a drive unit 32. The drive unit travels upon a flexible track 34 that is secured by releasable mounts in the form of magnets 36 to the interior surface of the tank shell of a railroad tank car. Alternative track releasable mounts, such as suction devices, may be substituted for the magnets. The track is oriented so that the probe trolley passes over one of the circumferential girth welds, a portion of which is indicated at 38 in phantom, of the tank shell. As illustrated, the track 34 extends so that the drive unit traverses an arcuate path along the bottom and side portions of the tank shell. As a result, when the drive unit is activated, the probe trolley scans the portion of the weld that is subjected to the highest stresses, typically a four to eight foot section, that is, two to four feet extending in each direction from the tank shell bottom longitudinal centerline.

Drive units and tracks of the type illustrated at 32 and 34 in FIG. 1 are known in the art. For example, a suitable drive unit and track system may be obtained from Bug-O Systems of Pittsburgh, Pa. Such drive units come equipped with a clamping mechanism (as illustrated at 31 in FIG. 1) that allows the position of a tool (such as probe trolley 32) to be adjusted or "fine-tuned" after the track is secured to a surface and the drive unit is positioned upon the track.

Drive unit 32 may alternatively take the form of a remote-controlled or preprogrammed computer-controlled device that moves the probe trolley along at a fixed distance from the weld without the assistance of track 34. Such a drive unit, for example, could take the form of a small vehicle, a geared mechanism, a suspended mechanism or a movable support structure (such as a swinging arm). In such instances, track 34 could be eliminated. The drive unit could also take the form of a device that is moved manually. For example, the drive unit could be a small vehicle that a technician moves by hand along a weld, either with or without a track.

As will be described in greater detail below, the probe trolley 30 communicates with an instrument rack 44 via cables 46. In addition, a pump 48 supplies coupling fluid (usually water) from a supply 50 to the probe trolley via flexible hose 52 (see also FIG. 2). The instrument rack and coupling fluid supply are supported upon wheeled cart 54. The wheeled cart remains outside of the tank. The instrument rack contains a monitor 56, a retractable keyboard 58 and a five-channel computer processor 60. A heating unit 62 is positioned on the top or side of the instrument rack to allow cold weather operation of the system. A remote display and mouse 64 may optionally be connected to the instrument rack. This remote display and mouse may be positioned within the tank for use by the technician operating the drive unit and probe trolley.

Figure 2:
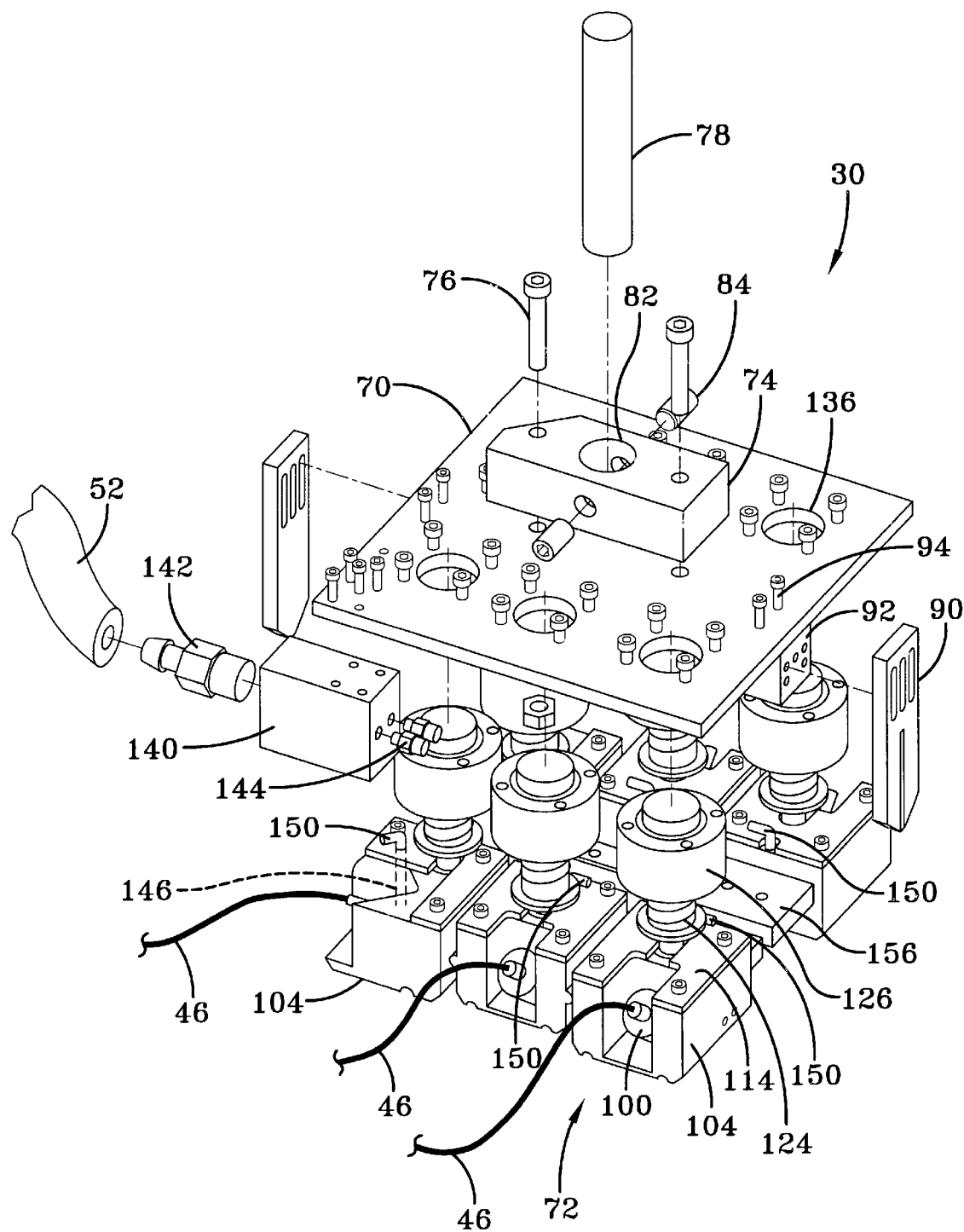
FIG. 2 is an enlarged and exploded perspective view of the probe trolley of FIG. 1.

Turning to FIG. 2, the details of the probe trolley 30 are shown. The trolley features a top plate 70 to which is attached six probe mounting assemblies. One of the probe mounting assemblies is illustrated in general at 72 in FIGS. 2 and 3. A post mounting bracket 74 is secured to the top of the plate via fasteners 76 and features a recess 82 sized and shaped to receive post 78. The bottom portion of post 78 is secured within recess 82 via set screws 84. The top portion of post 78 is secured within the drive unit clamping mechanism (31 in FIG. 1).

A pair of weld alignment indicators 90 are mounted to the bottom surface of the top plate 70 via mounting blocks 92 and fasteners 94. The technician uses the indicators to properly align the trolley, and therefore the six probes, with the weld by manipulating the drive unit clamping mechanism (31 in FIG. 1).

Figure 3:
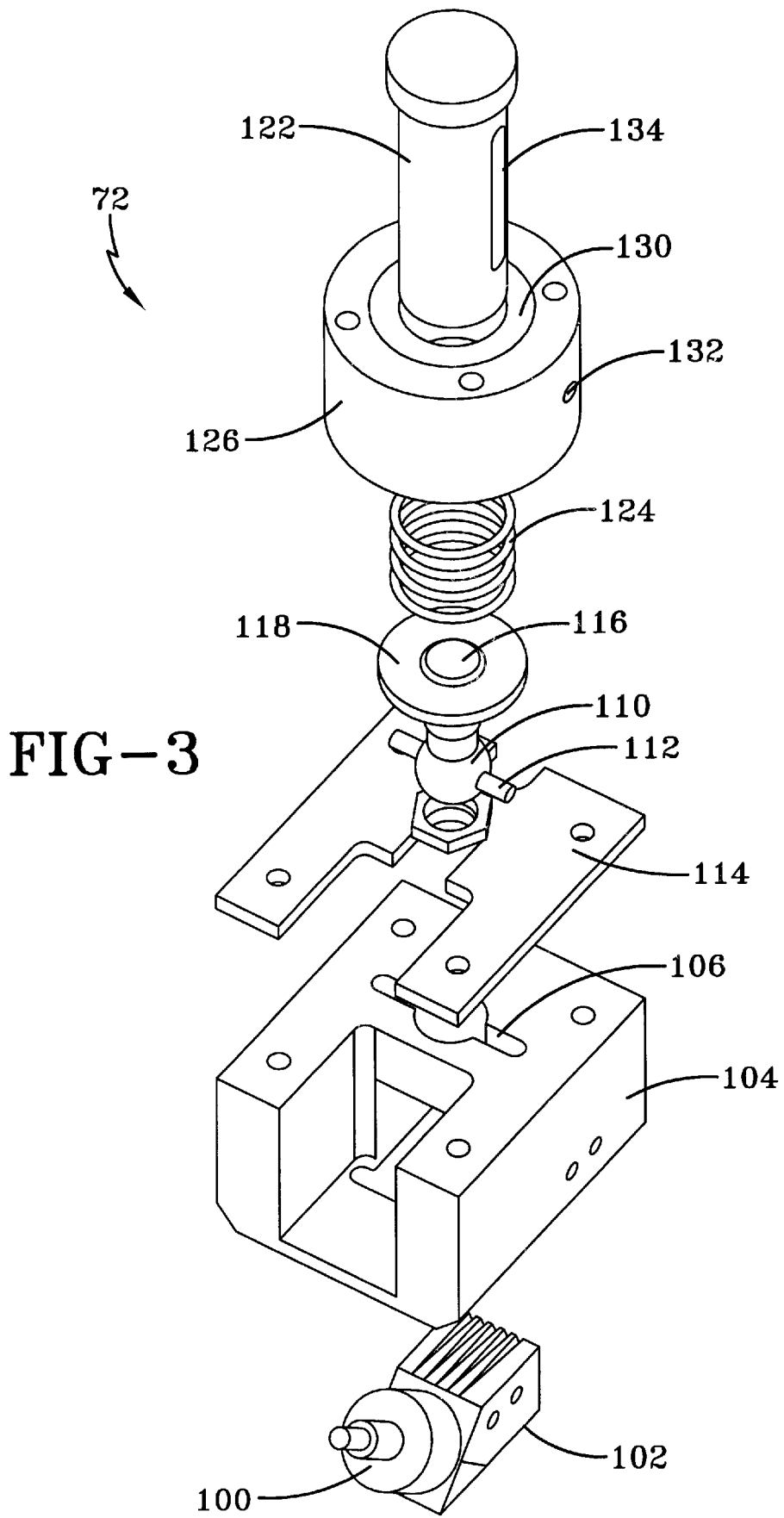
FIG. 3 is an enlarged exploded perspective view of one of the probe mounting assemblies of FIG. 2.

The components of a probe mounting assembly 72 are illustrated in FIG. 3. Each transducer or probe 100 is mounted to a wedge 102. As a result, the probe is held at the optimal scanning angle with respect to the surface being scanned. The wedge is secured within a probe shoe 104 in a removable fashion. As a result, wedges may be exchanged so that the probe angle may be selected based upon the thickness of the weld and tank wall being scanned. The probe shoe features an aperture 106 that receives a swivel ball 110 and pin 112. The swivel ball and pin are trapped within the probe shoe 104 via plate 114. As a result, the probe shoe, and therefore the probe, is free to pivot slightly about any axis.

The swivel ball is connected to a shaft 116 having a threaded top portion. A washer 118 is threaded onto the shaft 116. Shaft 116 is then screwed into a recess in the bottom of a piston 122 so that a compression coil spring 124 is trapped between the washer and a bearing holder 126. A bearing 130 is housed within the bearing holder and guides the vertical movement of the piston. A set screw (not shown) is inserted through an aperture 132 in the bearing holder and engages a slot 134 in the piston 122 so that the vertical travel of the piston is restricted.

Figure 6:
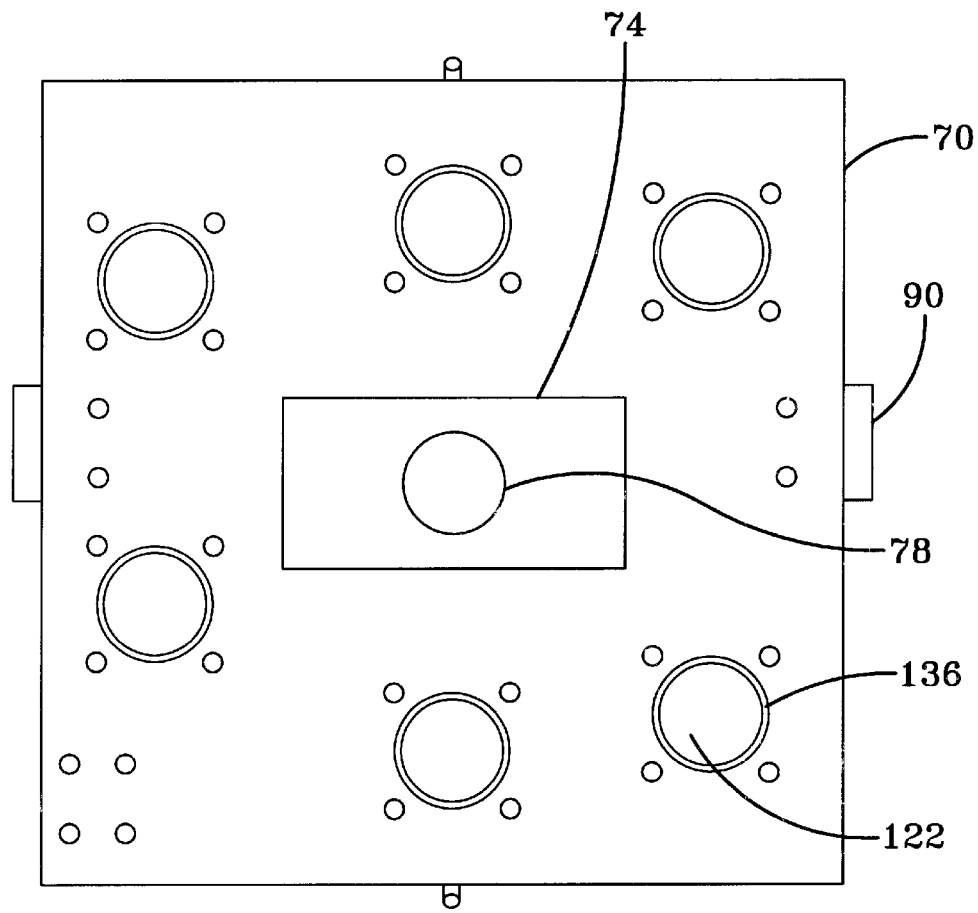
FIG. 6 a top plan view of the probe trolley of FIG. 2 as assembled.

The bearing holder 126 is secured to the trolley top plate 70. As illustrated in FIGS. 2 and 6, the trolley top plate features six apertures 136 sized to accommodate the pistons of the six probe mounting assemblies. As a result, the probe shoes, and therefore the probes, of each probe mounting assembly are free to travel vertically to a limited extent under the effect of the compression coil springs 124.

As shown in FIG. 2, coupling fluid is supplied to the probe trolley 30 via a flexible hose 52. The type of coupling fluid used depends upon the environment. Water is one type of coupling fluid that may be used. A fluid fitting block 140 is mounted to the bottom of the trolley top plate and receives large fluid fitting 142. The large fluid fitting 142 engages hose 52 and communicates with smaller fluid fittings 144 via passages within fluid fitting block 140. Each probe shoe 104 of the six probe mounting assemblies features a passage 146 that exits the bottom of the probe shoe and features a fluid fitting 150 at its top end. A network of flexible tubing (not shown) extends between the two fluid fittings 144 on the fluid fitting block and the six probe shoe fluid fittings 150. As a result, fluid is distributed through the bottom of each of the six probe shoes 104.

Figure 5:
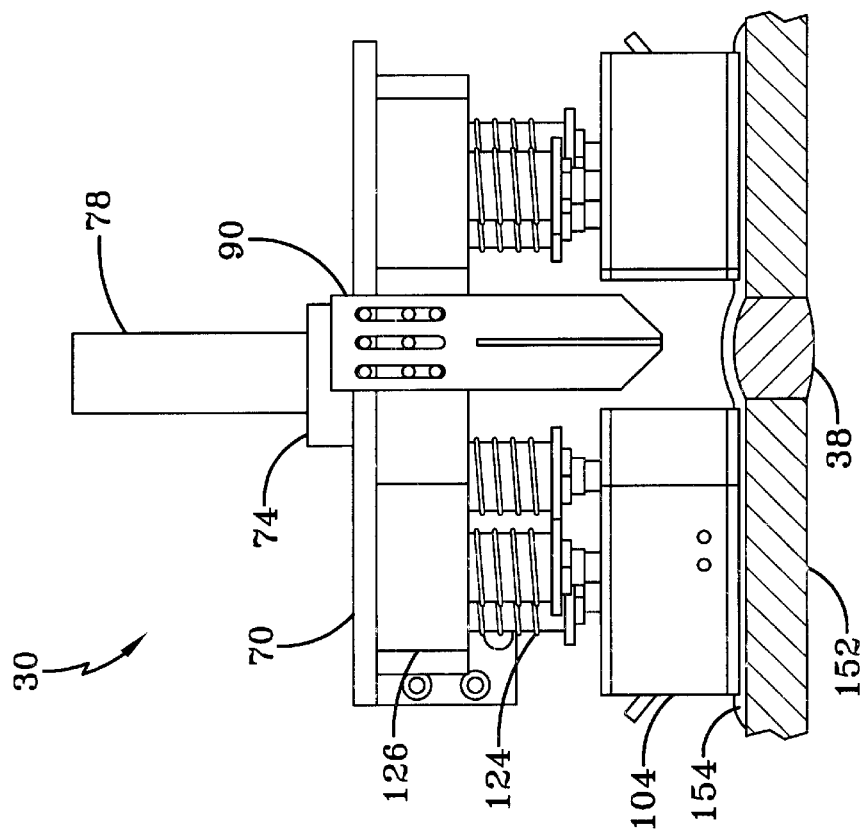
FIG. 5 a front elevation view of the probe trolley of FIG. 2 as assembled.
Figure 4:
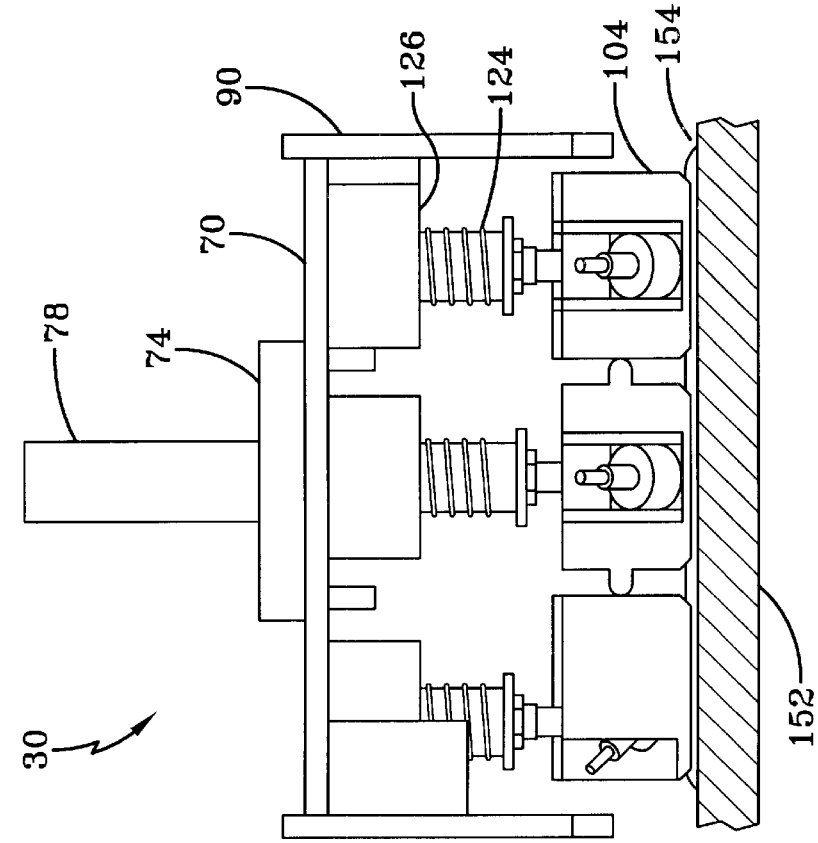
FIG. 4 is a side elevation view of the probe trolley of FIG. 2 as assembled.

FIGS. 4 and 5 illustrate the proper orientation of the probe trolley 30 with respect to the wall 152 of a tank shell and a circumferential girth weld 38. Note that for the sake of clarity, the coupling fluid supply system components are not shown in FIGS. 4–6. As the probe trolley is moved along the weld, via the track and drive unit of FIG. 1, the six probe shoes 104 straddle the weld and travel a short distance above the tank shell walls on both sides of the weld. As the probe trolley is moved along the weld, the coupling fluid passes through the bottom of the probe shoes and fills the space between the probe shoes and the tank wall. Due to the combined action of the coil springs 124 and swivel balls (110 in FIG. 3) of the probe mounting assemblies, the probe shoes in effect "float" on the coupling fluid along the tank wall. In other words, a layer of coupling fluid 154 maintains contact with both the bottom of the probe shoes and the tank wall at all times. As a result, wear to the probes, probe shoe and tank inner wall is minimized. As indicated at 156 in FIG. 2, brushes may optionally be attached to the inner surfaces of the probe shoes to control or eliminate turbulence during the formation of the coupling fluid layer 154.

As indicated in FIGS. 1 and 2, cables 46 run between each probe 100 and the equipment rack 44. As a result, each probe is in communication with the five-channel computer processor indicated at 60 in FIG. 1. The five-channel computer processor 60 is an ultrasonic instrument that energizes the probes so that they direct ultrasonic energy in the form of waves through the coupling fluid and into the tank wall and weld. Processor 60 receives and analyzes the signals that it receives from the probes in response to reflected ultrasonic beams. Suitable ultrasonic instruments and probes include the Krautkramer USPC 2100 ultrasonic system, available from Krautkramer Branson, Inc. of Lewistown, Pa.

Figure 7:
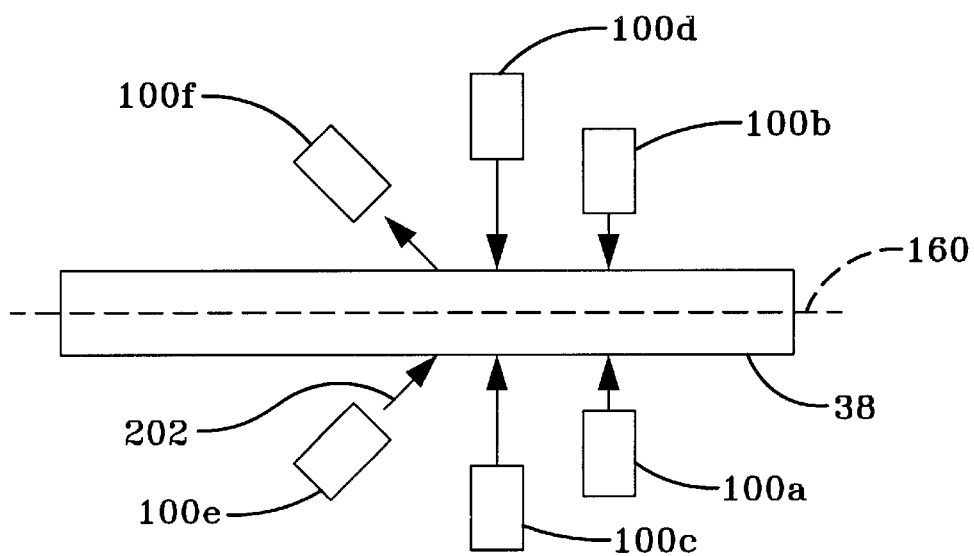
FIG. 7 is a top schematic view showing the orientation of the four angle beam probes and the pair of transverse probes of the ultrasonic testing system of FIG. 1.

The orientations of the six transducers or probes 100 with respect to circumferential girth weld 38 are illustrated in FIG. 7. More specifically, four angle beam probes are positioned as indicated at 100*a*–100*d*. These four probes are used to detect longitudinal defects in weld 38, that is, defects or flaws that run generally parallel to the longitudinal axis of the weld, indicated in phantom at 160. A transmitting and receiving pair of probes are positioned as indicated at 100*e* and 100*f* respectively, so that transverse defects, that is, defects or flaws that run substantially perpendicular to weld longitudinal axis 160, may also be detected.

Figure 8:
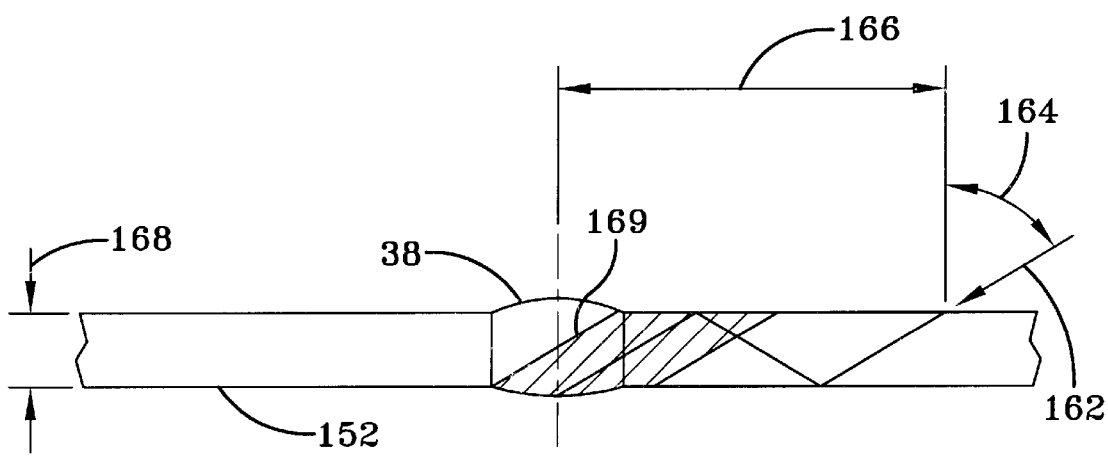
FIG. 8 is a sectional view of a portion of the tank wall and the weld showing an example of the transmission path of the ultrasonic beam emitted by one of the angle beam probes of FIG. 7.

FIG. 8 shows the transmission path 162 of an ultrasonic beam emitted by probe 100*a*. The beam 162 transmitted from the probe is projected through the coupling fluid layer (154 in FIGS. 4 and 5) into the tank wall at an angle of incidence 164 and is reflected by the inner and outer surfaces of the tank wall so as to focus on the center of the outer surface of the weld. As a result, the portion of the weld 38 indicated at 169 is scanned for longitudinal defects. Any longitudinal defect encountered by the ultrasonic beam in this portion of the weld will reflect the beam back along the same path to be received by the probe 100*a*. The appropriate angle 164 is determined based upon the thickness of the tank wall 168 and the distance 166 between the weld center and the point that the ultrasonic beam enters the tank wall. Typical values for these dimensions, presented as examples only, are an angle of incidence of approximately 60° when the distance 166 is approximately 2.36" and the tank thickness (168) is approximately 0.44".

Figure 9:
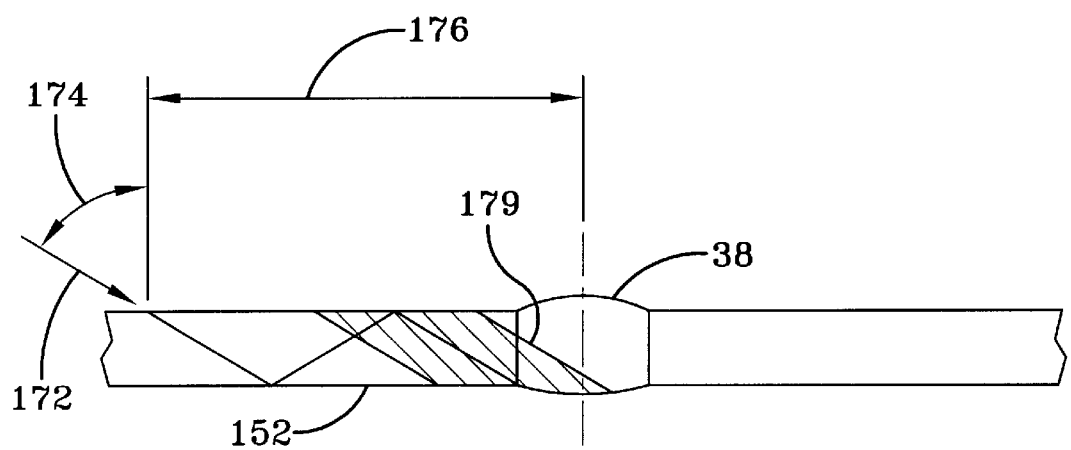
FIG. 9 is a sectional view of a portion of the tank wall and the weld showing an example of the transmission path of the ultrasonic beam emitted by another one of the angle beam probes of FIG. 7.

As illustrated in FIG. 9, the transmission path 172 of the ultrasonic beam of probe 100*b* is directed to focus on the left edge of the outer surface of the weld. As a result, the portion 179 of the weld 38 is scanned for longitudinal defects. Continuing with the example of a tank wall thickness of approximately 0.44", sample values for angle of incidence 174 and distance 176 for probe 100*b* are approximately 60° and 2.67", respectively.

Figure 10:
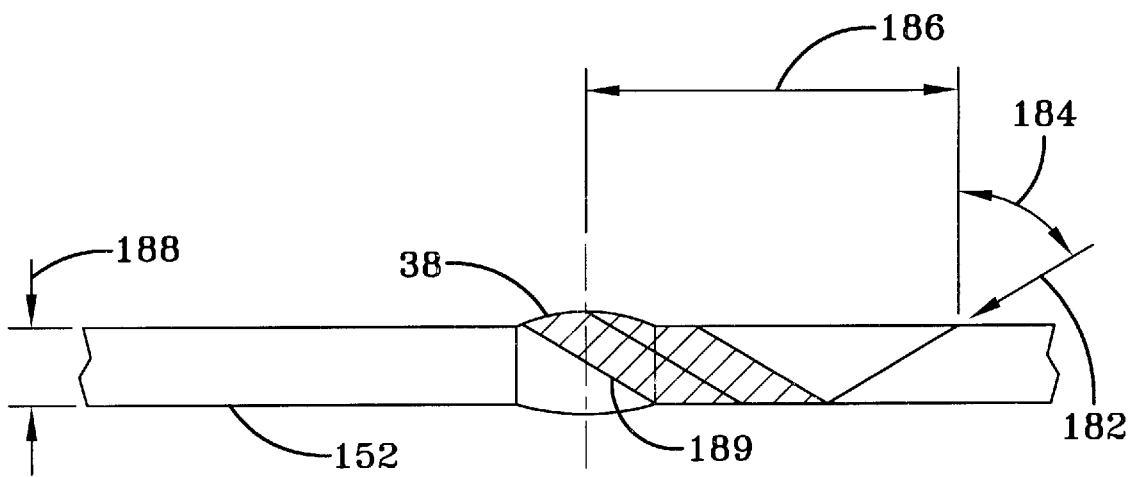
FIG. 10 is a sectional view of a portion of the tank wall and the weld showing an example of the transmission path of the ultrasonic beam emitted by another one of the angle beam probes of FIG. 7.
Figure 11:
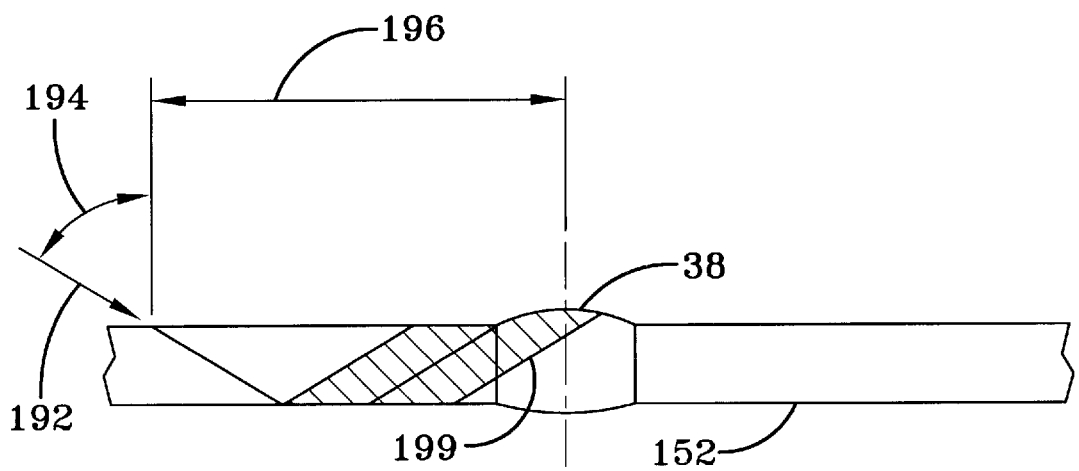
FIG. 11 is a sectional view of a portion of the tank wall and the weld showing an example of the transmission path of the ultrasonic beam emitted by another one of the angle beam probes of FIG. 7.

FIGS. 10 and 11 show the ultrasonic beam transmission paths for probes 100*c* and 100*d* at 182 and 192, respectively. The spacing 186 and angle of incidence 184 for ultrasonic beam 182 is chosen so that it focuses on the center of the inner surface of the weld. As a result, weld portion 189 is scanned for longitudinal defects. The spacing 196 and angle of incidence 194 of ultrasonic beam 192 is chosen so that it focuses on the left edge of the inner surface of the weld. As a result, weld portion 199 is scanned for longitudinal defects. Sample values for dimensions 184 and 186 are approximately 60° and 1.68", respectively, and for dimensions 194 and 196, 60° and 1.91", respectively.

Figure 12:
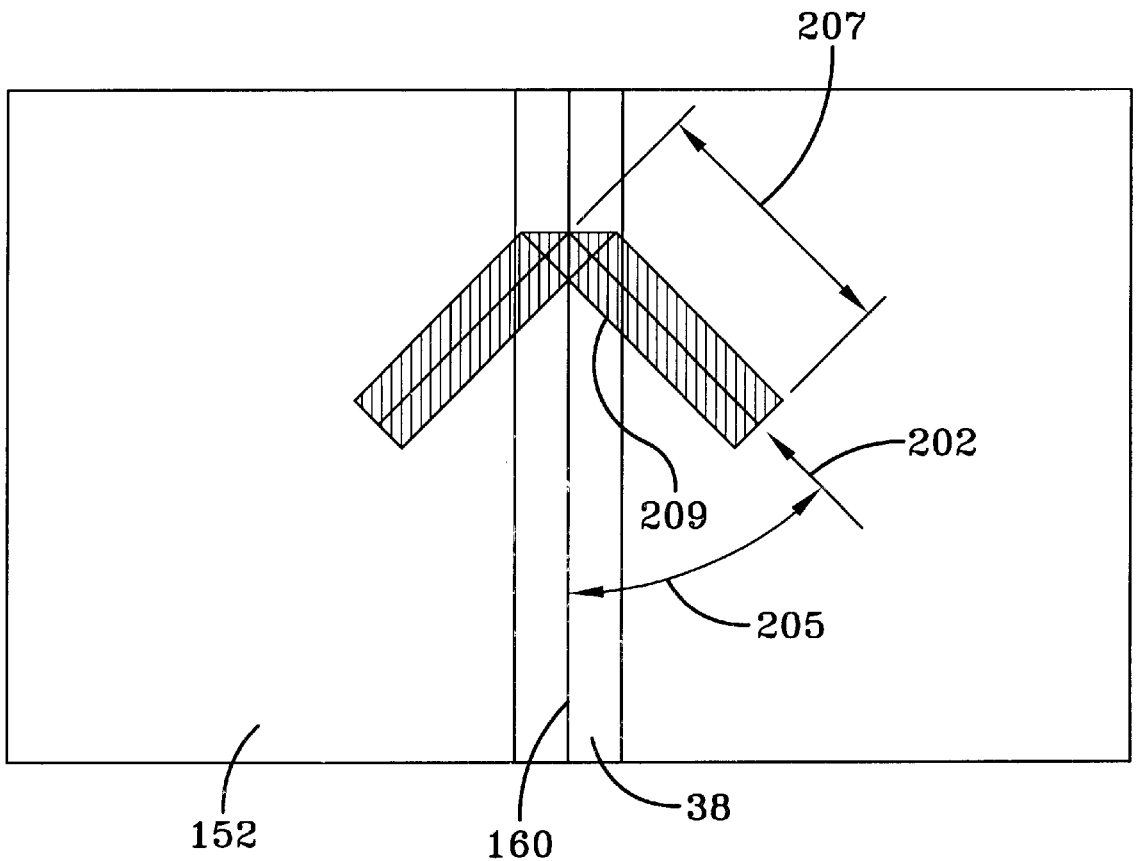
FIG. 12 is a top plan view of a portion of the tank wall and the weld showing an example of the transmission path of the ultrasonic beam transmitted and received by the pair of transverse probes of FIG. 7.
Figure 13:
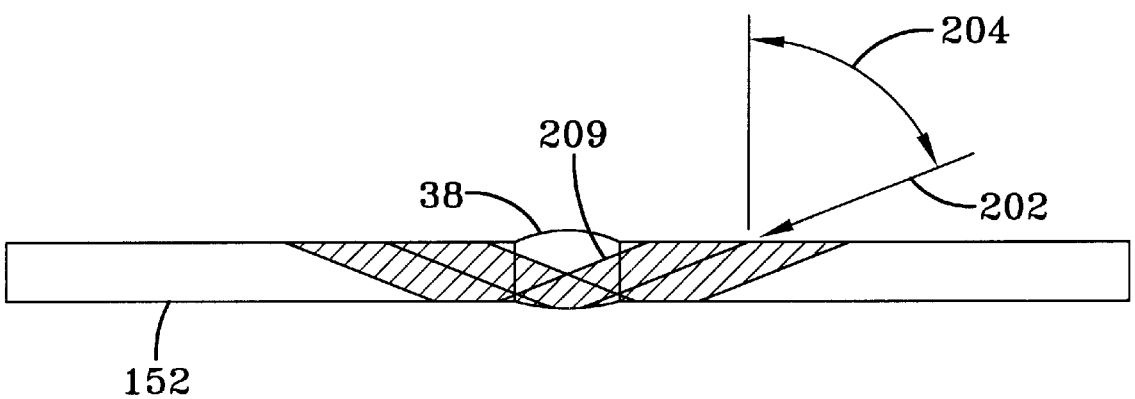
FIG. 13 is a sectional view of a portion of the tank wall and the weld showing an example of the transmission path of the ultrasonic beam transmitted and received by the pair of transverse probes of FIG. 7.

The transmission path of the ultrasonic beam transmitted by probe 100*e* and received by probe 100*f* is illustrated in FIGS. 12 and 13 at 202. The ultrasonic beam 202 enters the tank wall at incidence angles 204 and 205 and is reflected at the center of the outer surface of the weld and passes out of the weld and back out through the inner surface of the tank wall as illustrated. As a result, the portion of the weld indicated at 209 is scanned for transverse defects. Any transverse defect encountered by the ultrasonic beam in this portion of the weld is reflected along the path illustrated to be received by the probe 100*f*. Sample values for angles 204 and 205 are 75° and 45°, respectively with a distance 207 of approximately 1.98".

The operation of the system of the present invention will now be discussed with reference to FIG. 1. A technician first positions the track 34 so that it runs parallel to a circumferential girth weld 38. The technician next places the drive unit 32 upon one end of the track and, with the assistance of the weld alignment indicators 90 (FIGS. 2 and 5), adjusts the clamping mechanism 31 so that the probe trolley 30 is properly aligned with the weld. The system is then calibrated. The technician may perform this task from inside the tank by using the remote display and mouse 64.

Once the system is set up and calibrated, the first scan of the weld may be performed. The technician activates the drive unit 32 so that it travels from one end of the track to the other. As a result, the probe trolley 30 makes one pass or sweep over the weld. The drive unit shuts off automatically when it reaches the opposite end of the track. The scanning speed of the system is approximately 2 inches per second. It therefore takes the drive unit approximately 30 seconds to travel from one end of the track to the other.

When the drive unit reaches the other end of the track, the technician loosens the clamping mechanism 31 and rotates the probe trolley 180°. After re-tightening the clamping mechanism, and re-calibrating the system (if necessary), the technician activates the drive unit so that a second pass or sweep is made over the weld by the probe trolley. By making two such sweeps or passes, the weld is, in effect, scanned by twelve probe positions. That is, during the first pass, the portions of the welds indicated in FIGS. 8–13 are scanned for defects. During the second pass, the portions of the weld indicated by mirror images of FIGS. 8–13 are scanned. As a result, the weld is subjected to several scanning patterns in just two 30 second passes.

As the probe trolley passes over the weld, the probes are energized and test information is received by processor 60 for the length of the weld inspected. More specifically, the probes send thousands of synchronized pulses of sound through the tank wall and weld. These signals or beams are reflected and sent to processor 60. Processor 60 analyzes the data using time of flight defraction techniques and displays the resulting information on the monitor screen 56 (and 64) in the form of five zones, one zone for each of the four probes 100a–100d (FIG. 7) and one zone for probes 100e and 100f. Each zone displays information in the form of a moving strip chart where the signal amplitude from the probe(s) is plotted on the Y-axis and the distance along the weld is represented by the X-axis. A prematurely reflected beam, which occurs when a beam is reflected off of a flaw or defect, gives a spike on the monitor. The processor is configured to send an alarm signal when a spike has an amplitude greater than a predetermined limit. An alarm indicates that the corresponding portion of the weld warrants further inspection for the presence of weld surface or sub-surface defects or flaws such as cracks, inclusions, laminations or the like.

Test information for a weld is stored by processor 60 for future playback and historical documentation. The test data may also be printed out or transmitted to an off-site laboratory for further analysis.

While the preferred embodiments of the invention have been shown and described, it will be apparent to those skilled in the art that changes and modifications may be made therein without departing from the spirit of the invention, the scope of which is defined by the appended claims.

What is claimed is:

1. An ultrasonic testing system for inspecting a weld comprising:
   a) a probe trolly;
   b) a plurality of probes, oriented at a plurality of angles to the weld emitting and receiving ultrasonic energy, mounted to said probe trolley;
   c) a motorized drive unit to which said probe trolley is adjustably secured for movement therewith;
   d) a track included releasable mounts for temporarily securing the track to a surface adjacent to the weld, said drive unit adapted to travel upon said track; and
   e) a weld alignment indicator to align the probe assembly over the weld so that the some of the plurality of probes are positioned along an edge adjacent to the weld and on either side of the weld;
   whereby said probe trolley may be positioned relative to said drive unit and weld so that said plurality of probes scan the weld when said drove unit is positioned upon said track and activated to travel there along.

2. The ultrasonic testing system of claim 1 further comprising a computer in communication with said plurality of probes so that data from said probes may be collected and analyzed.

3. The ultrasonic testing system of claim 2 further comprising a monitor in communication with said computer processor so that data collected from said probes and analyzed may be displayed.

4. The ultrasonic testing system of claim 1 further comprising a system for delivering fluid to said probe trolley so that a layer of fluid for coupling energy is formed between said probes and the surface adjacent to the weld.

5. The ultrasonic testing system of claim 4 wherein said system for delivering fluid includes:
   a) a supply of coupling fluid;
   b) a flexible hose extending between said supply of coupling fluid and said probe trolley; and
   c) a pump for transferring coupling fluid from the supply of coupling fluid through said flexible hose to said probe trolley.

6. The ultrasonic testing system of claim 1 wherein said probe trolley includes a top plate and each of said probes is mounted to said top plate via a probe mounting assembly.

7. The ultrasonic testing system of claim 6 wherein said probe mounting assembly includes:
   a) a bearing holder secured to said top plate;
   b) a bearing disposed within said bearing holder;
   c) a piston slidably received in said bearing;
   d) a probe shoe for holding a probe;
   e) said probe shoe attached to said piston so that said probe shoe may float upon a layer of coupling fluid disposed between the probe and the surface adjacent to the weld.

8. The ultrasonic testing system of claim 6 wherein the weld indicator is attached to said top plate so that said probe trolley and the probes mounted thereon may be properly aligned with the weld to be inspected.

9. A probe trolley for ultrasonic testing of a weld comprising:
   a) a top plate having a top surface and a bottom surface;
   b) a plurality of ultrasonic probes;
   c) a weld alignment indicator mounted to the bottom surface of the top plate to align the probe trolley over the weld so that the some of the plurality of probes are positioned along an edge adjacent to the weld and on either side of the weld; and
   d) means for securing said top plate to a drive system so that the probe trolley may be propelled along the weld; whereby the plurality of probes attached to said top plate and oriented on either side of the weld to scan the weld as the probe trolley is propelled along the weld.

10. The probe trolley of claim 9 wherein said probes are moveably mounted to said top plate.

11. The probe trolley of claim 9 further comprising at least one flexible hose for providing a fluid to said probes so that a layer of fluid for coupling energy is formed between said probes and a surface adjacent to the weld.

12. The probe trolley of claim 9 wherein said probes are mounted to said top plate by probe mounting assemblies, each said probe mounting assembly including:
   a) a bearing holder attached to said top plate;
   b) a bearing disposed in said bearing holder;

c) a probe shoe for holding a probe; and d) a piston slidably disposed in said bearing, said probe shoe attached to said piston.

13. The probe trolley of claim 12 wherein said probe is mounted to a wedge and said wedge is removably held by the probe shoe so that the probe is held at a desired angle relative to a surface adjacent to the weld.

14. The probe trolley of claim 12 wherein the mounting assemblies each include a compression spring positioned between said top plate and each probe shoe so that said probe shoes maintain contact with the surface adjacent to the weld.

15. The probe trolley of claim 12 wherein said probe shoes are mounted to said pistons by swivel balls so that said probe shoes may pivot slightly.

16. The probe trolley of claim 9 wherein the weld indicator is attached to said top plate so that the probe trolley may be properly aligned with the weld.

17. An ultrasonic testing system for inspection a weld comprising:

a) a probe trolley;

b) a plurality of probes, oriented at a plurality of angles to the weld emitting and receiving ultrasonic energy, mounted to said probe trolley;

c) a device for moving said probe trolley at a fixed radial distance from the weld so that said plurality of probes scan the weld; and d) a weld alignment indicator to align the probe assembly over the weld so that the some of the plurality of probes are positioned along an edge adjacent to the weld and on either side of the weld.

18. The ultrasonic testing system of claim 17 further comprising a system for delivering fluid to said probe trolley so that a layer of fluid for coupling energy is formed between said probes and a surface adjacent to the weld.

19. A method for ultrasonically testing a circumferential girth weld of a tank comprising the steps of:

a) positioning a track along the weld on an inner surface of the tank;

b) attaching a plurality of probes to a drive unit;

c) placing the drive unit on the track;

d) activating the drive unit so that it travels along the track so that the probes can scan the weld;

e) collecting data from the probes; and f) analyzing the data from the probes to determine if defects are present in the weld.

20. The method of claim 19 further comprising the steps of:

g) rotating the plurality of probes after an initial scan of the weld is performed; and h) performing a second scan of the weld in a reverse direction.

21. The method of claim 19 wherein the tank is a tank of a railroad tank car.

* * * * *

UNITED STATES PATENT AND TRADEMARK OFFICE
CERTIFICATE OF CORRECTION

PATENT NO.    : 6,530,278 B1         Page 1 of 1
DATED         : March 11, 2003
INVENTOR(S)   : Matthew D. Bowersox et al.

It is certified that error appears in the above-identified patent and that said Letters Patent is hereby corrected as shown below:

<u>Column 7,</u>
Line 60, "that the some of the plurality of probes" should read -- that some of the plurality --.

<u>Column 8,</u>
Line 47, "that the some of the plurality of probes" should read -- that some of the plurality --.

<u>Column 9,</u>
Line 30, "that the some of the plurality of probes" should read -- that some of the plurality --.

Signed and Sealed this

Ninth Day of September, 2003

JAMES E. ROGAN
*Director of the United States Patent and Trademark Office*